United States Patent
Kirkemo (10) Patent No.: US 10,918,412 B2
(45) Date of Patent: Feb. 16, 2021

(54) SURGICAL GUIDANCE DEVICES, METHODS, AND SYSTEMS

(71) Applicant: Boston Scientific Scimed, Inc., Maple Grove, MN (US)

(72) Inventor: Aaron Kurtiss Kirkemo, Gladstone, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 914 days.

(21) Appl. No.: 15/379,608

(22) Filed: Dec. 15, 2016

(65) Prior Publication Data
US 2017/0172619 A1 Jun. 22, 2017

Related U.S. Application Data

(60) Provisional application No. 62/269,584, filed on Dec. 18, 2015.

(51) Int. Cl.
| | | |
|---|---|---|
| A61B 17/34 | (2006.01) |
| A61B 6/12 | (2006.01) |
| A61B 90/11 | (2016.01) |
| A61B 90/50 | (2016.01) |
| A61B 34/20 | (2016.01) |

(Continued)

(52) U.S. Cl.
CPC ............ *A61B 17/3403* (2013.01); *A61B 6/12* (2013.01); *A61B 34/20* (2016.02); *A61B 90/11* (2016.02); *A61B 90/50* (2016.02); *A61B 2017/3407* (2013.01); *A61B 2017/3411* (2013.01); *A61B 2090/3937* (2016.02); *A61B 2090/3966* (2016.02); *A61B 2090/571* (2016.02)

(58) Field of Classification Search
CPC ............ A61B 17/3043; A61B 17/3417; A61B 2017/3411; A61B 2017/3407; A61B 2017/3405; A61B 2017/3409; A61B 2017/3413; A61B 2017/00455; A61B 34/20; A61B 90/11; A61B 90/39; A61B 9/50; A61B 2090/3966; A61B 2090/3937; A61B 209/571; A61B 6/12; A61M 5/427
See application file for complete search history.

(56) References Cited

U.S. PATENT DOCUMENTS 4,750,487 A 6/1988 Zanetti
5,056,523 A * 10/1991 Hotchkiss, Jr. .... A61B 17/3403
378/37

(Continued)

FOREIGN PATENT DOCUMENTS

WO WO 2015/138883 9/2015

*Primary Examiner* — Darwin P Erezo
*Assistant Examiner* — Erin L Colello
(74) *Attorney, Agent, or Firm* — Bookoff McAndrews, PLLC (57) ABSTRACT

A device for improving the efficiency and safety of medical imaging in a medical procedure is disclosed. The device may have a shaft extending along a shaft axis. The shaft may have at least two markers spaced along the shaft axis and a blade extending along the shaft axis. The device may have a needle guide extending away from the shaft along a needle guide axis transverse with the shaft axis. The needle guide may have at least one guide structure offset from the shaft axis along the needle guide axis. Each guide structure may be adapted to receive a needle in a direction parallel to the shaft axis. Related methods and systems are disclosed.

20 Claims, 10 Drawing Sheets

(51) Int. Cl.
*A61B 90/00* (2016.01)
*A61B 90/57* (2016.01)

(56) References Cited

U.S. PATENT DOCUMENTS

| | | | | |
|---|---|---|---|---|
| 5,743,916 A * | 4/1998 | Greenberg | ............ | A61B 17/02 606/102 |
| 6,673,060 B1 * | 1/2004 | Fleming, III | ......... | A61M 1/008 600/149 |
| 6,689,142 B1 | 2/2004 | Tremaglio, Jr. et al. | | |
| 7,083,624 B2 * | 8/2006 | Irving | ................ | A61B 17/157 606/87 |
| 7,575,578 B2 * | 8/2009 | Wetzler | ................ | A61B 17/17 606/96 |
| 8,273,091 B2 * | 9/2012 | Elghazaly | .......... | A61B 17/1725 606/96 |
| 8,771,283 B2 * | 7/2014 | Larsen | ............... | A61B 17/1725 606/96 |
| 9,232,977 B1 * | 1/2016 | Rehman | ................ | A61B 90/11 |
| 10,357,314 B2 * | 7/2019 | Cocaign | ................ | A61B 90/06 |
| 2003/0220651 A1 * | 11/2003 | Pusnik | ................ | A61B 17/1725 606/98 |
| 2005/0177171 A1 * | 8/2005 | Wetzler | ................ | A61B 17/17 606/96 |
| 2005/0177211 A1 * | 8/2005 | Leung | ................ | A61B 18/148 607/101 |
| 2006/0064106 A1 * | 3/2006 | Fernandez | ......... | A61B 17/1703 606/98 |
| 2006/0064164 A1 * | 3/2006 | Thelen | ................ | A61B 17/164 623/16.11 |
| 2007/0093834 A1 * | 4/2007 | Stevens | .............. | A61B 17/1764 606/279 |
| 2008/0027457 A1 * | 1/2008 | Dienst | ................ | A61B 17/3403 606/96 |
| 2008/0039857 A1 * | 2/2008 | Giersch | ............ | A61B 17/1703 606/96 |
| 2008/0039866 A1 * | 2/2008 | Stetz | ...................... | A61B 90/11 606/129 |
| 2009/0093813 A1 * | 4/2009 | Elghazaly | .......... | A61B 17/1725 606/62 |
| 2011/0125157 A1 * | 5/2011 | Sharkey | ............. | A61B 17/8805 606/92 |
| 2011/0125159 A1 * | 5/2011 | Hanson | ............. | A61B 17/1764 606/96 |
| 2011/0125160 A1 * | 5/2011 | Bagga | ............... | A61B 17/1635 606/96 |
| 2011/0125200 A1 * | 5/2011 | Hanson | ................... | A61B 17/17 606/86 R |
| 2011/0125201 A1 * | 5/2011 | Hanson | ................... | A61B 90/11 606/86 R |
| 2012/0245645 A1 * | 9/2012 | Hanson | .............. | A61B 17/1764 606/86 R |
| 2013/0267960 A1 * | 10/2013 | Groh | ...................... | A61B 17/72 606/96 |
| 2014/0074117 A1 * | 3/2014 | Hanson | ............... | A61M 5/3287 606/130 |
| 2014/0343572 A1 * | 11/2014 | Windolf | ............ | A61B 17/1703 606/130 |
| 2014/0358087 A1 * | 12/2014 | Bunch | ................ | A61M 25/01 604/164.01 |

* cited by examiner

SURGICAL GUIDANCE DEVICES, METHODS, AND SYSTEMS

CROSS-REFERENCE TO RELATED PARAGRAPHS

This patent application claims the benefit of priority under 35 U.S.C. § 119 to U.S. Provisional Patent Application No. 62/269,584, filed Dec. 18, 2015, which is herein incorporated by reference in its entirety.

TECHNICAL FIELD

Aspects of the present disclosure generally relate to medical devices and procedures. In particular, some aspects related to surgical guidance devices, methods, and systems.

BACKGROUND

Medical imaging technologies, such as X-ray, are used within a variety of diagnostic and surgical procedures. These technologies allow a surgeon to visualize internal portions of a body without having to create a physical opening. In some procedures, these technologies are used to guide a surgical implementation, such as a needle, toward a targeted area of treatment, such as an organ. Percutaneous nephrolithonomy (or "PCNL"), for example, is one such procedure, wherein a needle is typically inserted through the body and into a kidney for removal of a kidney stone. Precise placement of the needle is required to avoid damaging the kidney. Therefore, medical imaging technologies are often used in PCNL procedures to both locate a kidney and track the location of the needle with respect to the located kidney.

Figure 1:
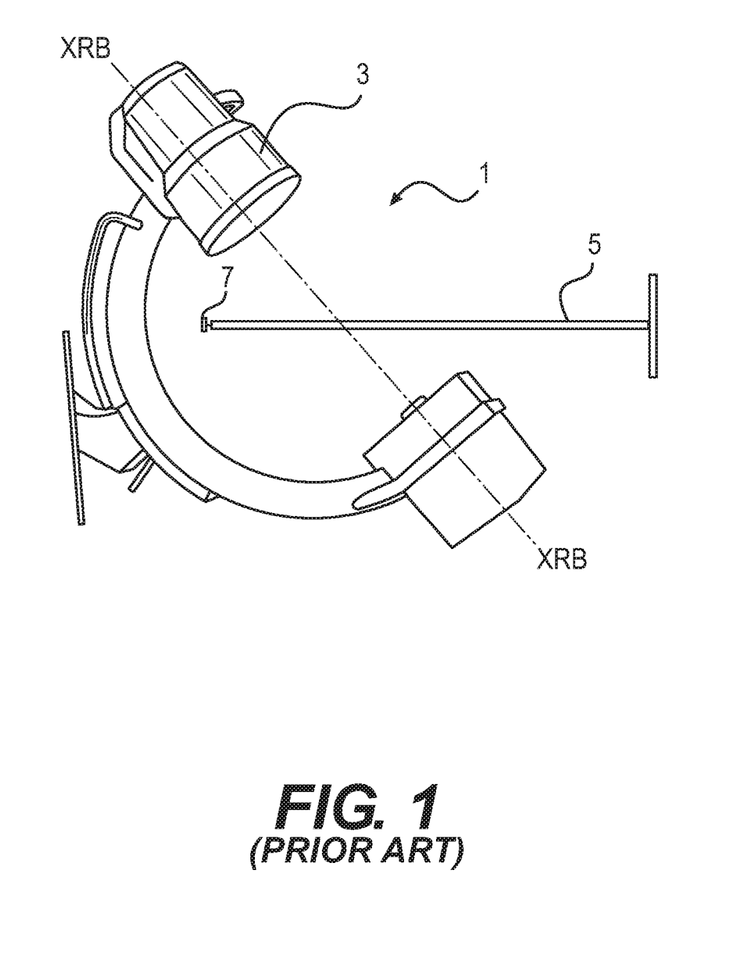
FIG. 1 depicts a prior art X-ray machine that is configured to capture an image of a body within at least one imaging plane.

Most imaging technologies can image the body within a single imaging plane. For X-ray technologies, the imaging plane is defined with respect to an X-ray beam. A prior art X-ray device 1 is shown in FIG. 1, which a skilled artisan would recognize as being similar to those made by Siemens®, Philips®, or like manufacturer. As shown, device 1 has a probe 3 that directs an X-ray beam along an X-ray beam axis XRB-XRB towards an operating table 5. During a PCNL procedure, a surgeon may locate a kidney by directing a first X-ray beam towards, for example, the coronal plane of the body. To guide the needle, a second X-ray beam may be directed toward, for example, the sagittal plane of the body. The resulting images may be used to located the kidney, provided they are coordinated to avoid parallax errors. Proper coordination is important; thus, a surgeon may spend a considerable amount of time working to reproducibly shift the X-ray beam between each plane.

Numerous images may be taken before the PCNL procedure can begin, each requiring the surgeon's time and attention. Additional images may be required during the procedure. For example, the needle may drift away from the kidney, requiring the surgeon to reimage the body. Some images are taken while the needle is at least partially inserted in the body. To avoid tissue damage, the surgeon must stabilize the needle for each image, often by hand. As a result, many images inadvertently capture a portion of the surgeon's hand. It is known that exposure to X-ray beams can cause cancer. Thus, aside from taking additional time, every additional image also poses a health risk for the surgeon.

Further improvements are required.

SUMMARY

Aspects of the present disclosure relate to surgical guidance devices, methods, and systems. Numerous aspects of the present disclosure are now described.

One aspect may be a guidance device, the device comprising: a shaft extending along a shaft axis, the shaft including a plurality of markers spaced along the shaft axis and an blade extending along the shaft axis; and a needle guide extending away from the shaft along a needle guide axis transverse with the shaft axis, the needle guide including at least one guide structure offset from the shaft axis along the needle guide axis, said structure being adapted to receive a needle in a direction parallel to the shaft axis.

This aspect may additionally and/or alternatively comprise one or more of the following features: the shaft and needle guide may be made of a radiolucent material while the plurality of markers are made of a radiopaque material; the shaft may include a hollow interior portion and the plurality of markers may be mounted in the hollow portion; the blade may be mounted in the hollow portion; the shaft may include a substantially rectangular perimeter coaxial with the shaft axis and a body facing surface located on a side of said perimeter; the needle guide may include a body facing surface that intersects the body facing surface of the shaft; the body facing surfaces of the shaft and needle may be joined by a fillet to form a continuous body facing surface; two of the plurality of markers may be located at opposite ends of the shaft; the blade may extend through each of the plurality of markers; each of the plurality of markers may include a perimeter coaxial with the shaft axis such that a first plane is defined by superimposing said perimeters along the shaft axis, the first plane being perpendicular to the shaft axis; each of the plurality of markers may comprise a plurality of concentric rings, each ring including a perimeter coaxial with the shaft axis; the at least one guide structure may have a guiding axis that is parallel to the shaft axis and transverse with the needle guide axis such that a second plane is defined by aligning the blade with the guiding axis, the second plane being parallel to the shaft axis; the at least one guide structure may have a circular entry sized to receive a needle along the guiding axis, and a cylindrical sidewall adapted to guide the needle the guiding axis; the at least one guide structure may comprise a plurality of guide structures spaced along the needle guide axis; and/or the device may further comprise a positioning arm attached to an interface portion of either of the shaft or the needle guide.

Without departing from this disclosure, this aspect may additionally and/or alternatively comprise one or more of the following features: a plurality of radiopaque hash marks may be disposed a regular intervals between each of plurality of markers; the shaft may include a substantially rectangular perimeter coaxial with the shaft axis and a body facing surface located on a side of said perimeter, the side being offset from the shaft axis along the needle axis; the shaft may have a first end and a second end, the first end being opposite of the second end along the shaft axis, wherein one of the plurality of markers is located at each of the first and second ends, such that a first plane is defined by aligning each of said perimeters along the shaft axis; the at least one guide structure may comprise a guiding axis that is parallel with the shaft axis and transverse with the needle guide axis, an entry with a perimeter that is coaxial with the guiding axis and sized to receive a needle along the guiding axis, and an interior sidewall that is coaxial with the central axis and adapted to guide the needle along the guiding axis; and/or a plurality of guide structures may be spaced apart at regular intervals along the needle guide axis, each interval may be marked by a hash mark.

Another aspect may be a guidance system, the system comprising: a guidance device including a shaft extending along a shaft axis, the shaft including at least one marker with a perimeter coaxial with a shaft axis, said perimeter including a width extending along shaft axis, and a blade extending along the shaft axis; a needle guide extending away from the shaft along a needle guide axis transverse with the shaft axis, the needle guide including at least one guide structure offset from the shaft axis along the needle guide axis, the structure being adapted to receive a needle along a guiding axis parallel to the shaft axis; and a positioning arm engageable with an interface portion of the guidance device, the arm being adapted to move the device relative to a body.

This aspect may additionally and/or alternatively comprise one or more of the following features: the shaft, the needle guide, and the positioning arm may be made of a radiolucent material, while the at least one marker and the blade are made of a radiopaque material; the shaft may include a substantially rectangular perimeter coaxial with the shaft axis and a body facing surface located on a side of said perimeter, wherein the needle guide has a body facing surface that intersects the body facing surface of the shaft to form a continuous body facing surface; the positioning arm may be moveable to place the continuous body facing surface adjacent or proximate to the body; the positioning arm may be adapted to fix the position of the guidance device relative to the body; and/or the system may further comprise one or more actuators attached to the positioning arm, each actuator being configured to move said arm.

Yet another aspect may be a guidance method, the method comprising: the step of positioning a guidance device adjacent a body, the device comprising: a shaft extending along a shaft axis, the shaft including a plurality of markers spaced along the shaft axis, and a blade extending along the shaft axis; and a needle guide extending away from the shaft along a needle guide axis transverse with the shaft axis, the needle guide including at least one guide structure offset from the shaft axis along the needle guide axis, said structure being adapted to receive a needle along a guiding axis parallel to the shaft axis; the step of defining a first plane by superimposing each of the least two markers along the shaft axis; the step of imaging the body the first plane; the step of inserting a needle into the at least one guide structure along the guiding axis; the step of defining a second plane by superimposing the blade with the needle along the needle guide axis; and/or the step of imaging the body in the second plane.

This aspect may additionally and/or alternatively comprise one or more of the following features: each of the plurality of markers may have a perimeter coaxial with the shaft axis, wherein the step of defining the first plane comprises superimposing each perimeter along the shaft axis; the method may further comprise the steps of positioning the shaft over a targeted area of treatment in the body, and inserting an operative end of the needle by a depth defined by imaging the body in the second plane; other steps may comprise placing a body facing surface of the guidance device against the body, and fixing the position of the guidance device relative to the body; and/or the step of positioning the guidance device may be performed by moving a positioning arm engaged with an interface portion of the guidance device.

It may be understood that both the foregoing summary and the following detailed descriptions are exemplary and explanatory only, neither being restrictive of the inventions claimed below.

BRIEF DESCRIPTION OF THE DRAWINGS

The accompanying drawings, which are incorporated in and constitute a part of this specification, illustrate exemplary embodiments that, together with the written descriptions, serve to explain the principles of this disclosure.

DETAILED DESCRIPTION

The present disclosure is now described with reference to exemplary embodiments of a surgical guidance device, system, and associated methods. Some embodiments are described with reference to a procedure incorporating a medical imaging technology. For example, some embodiments are depicted and/or described with reference to a PCNL procedure, wherein X-ray beams are utilized to detect the location of a kidney. Any reference to a particular procedure (such as PCNL), targeted area of treatment (such as a kidney), or medical imaging technology (such as X-ray) is provided for convenience and not intended to limit the present disclosure unless incorporated into the appended claims. Accordingly, the concepts and novelty underlying each embodiment may also be utilized for any analogous type of procedure, area of treatment, or imaging technology, medical or otherwise.

Numerous axes are described. In particular, a set of three directional axes, including an X-X axis, Y-Y axis, and Z-Z axis, are described. Each axis may be transverse, or even perpendicular, with the next so as to establish a coordinate system. The directional terms "proximal" and "distal" are similarly used to describe relative components and features. The term proximal refers to a position closer to the exterior of the body or a user, whereas the term distal refers to a position closer to the interior of the body or further away from the user. Each of these directional terms are provided for convenience and not intended to limit the present disclosure unless claimed.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. Unless stated otherwise, the term "exemplary" is used in the sense of "example," rather than "ideal."

Figure 2A:
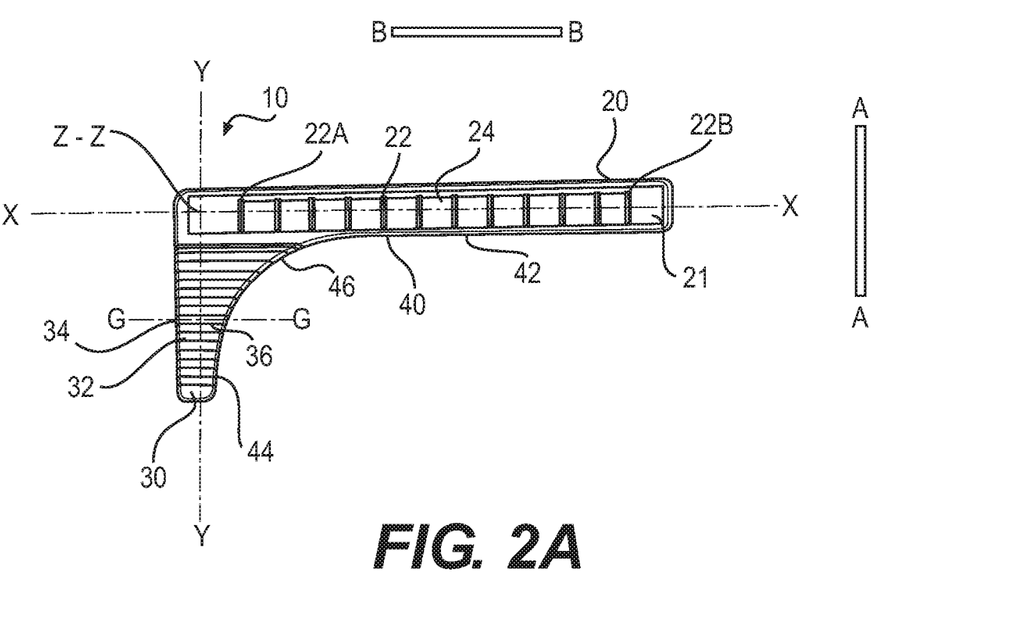
FIG. 2A depicts a side view of an exemplary guidance device in accordance with the present disclosure.

One embodiment of the present disclosure is depicted in FIG. 2A as a device 10 having a shaft 20 and a needle guide 30 extending away from shaft 20. Shaft 20 may have a substantially rectangular perimeter, of constant dimension, extending along a shaft axis X-X, whereas needle guide 30 may have a substantially rectangular perimeter, of varying dimension, extending along a needle guide axis Y-Y that is transverse with shaft axis X-X. In some embodiments, shaft axis X-X may be perpendicular to needle guide axis Y-Y, such that guide 30 extends substantially orthogonally to shaft 20. Shaft 20 and needle guide 30 are formed of a material that is transparent to one or more medical imaging technologies. For example, without limiting the present disclosure to a particular type of imaging technology, shaft 20 and guide 30 are described as radiolucent, that is, formed of a material that is transparent to X-rays, such as a polymeric material. Shaft 20 and guide 30 may also be visually transparent.

Figure 3A:
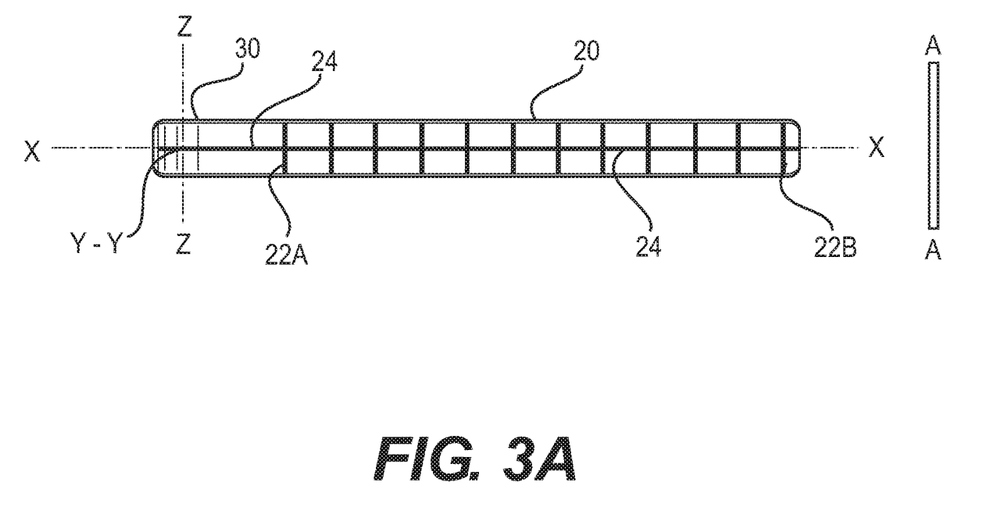
FIG. 3A depicts a top view of the device of FIG. 2A.
Figure 3B:
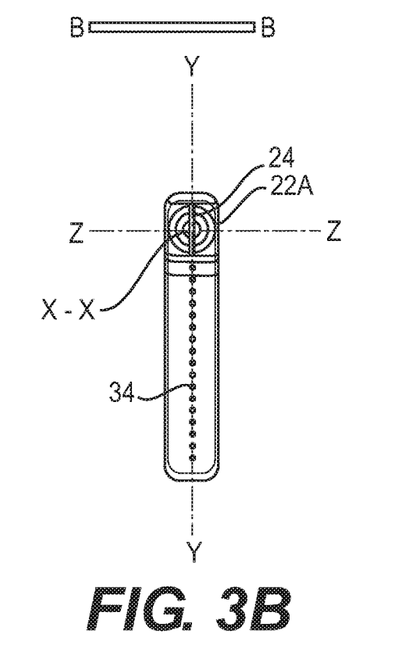
FIG. 3B depicts an end view of the device of FIG. 2A.

Shaft 20 of FIG. 2A has a plurality, or at least two, shaft markers 22 spaced along shaft axis X-X. Each marker 22 is formed of material that is opaque to one or more medical imaging technologies. For example, without limiting the present disclosure, each marker 22 is described below as being radiopaque, that is, formed of a material that is opaque to X-rays, such as a metal. Each marker 22 may also be visually opaque. Markers 22 define a first plane A-A (FIGS. 2A, 3A). Each marker 22 may be housed within an interior portion 21 of shaft 20 (FIG. 2A) and may include least one perimeter coaxial with shaft 20. As shown in FIG. 3B, for example, each marker 22 has a plurality of concentric rings, each ring having circular perimeter centered on shaft axis X-X. The two outermost markers 22 have been labeled as 22A and 22B, respectively. As shown in FIGS. 2A and 3A, the perimeter of at least markers 22A and 22B, for example, may be aligned to define first plane A-A as, in some embodiments, being perpendicular to shaft axis X-X.

First plane A-A is used to establish a relative difference between shaft 22 and a needle 50 (FIG. 2B) with respect to needle axis Y-Y. As shown in FIG. 3B, for example, first plane A-A is defined when each marker 22 is superimposed on the next along shaft axis X-X. First plane A-A may be defined by moving device 10 until any two markers 22 are superimposed along shaft axis X-X. To image first plane A-A, a probe 3 of an imaging device 1 (e.g., FIG. 1) is then placed in parallel therewith. Alternatively, because each marker 22 is radiopaque, first plane A-A may also be defined by capturing an image of device 10 in the general direction of shaft axis X-X, and then moving device 10 relative to probe 3, or vice versa, in a direction indicated by the image until the image of each markers 22 is superimposed along axis X-X.

At least one blade 24 extends along shaft axis X-X of shaft 20, as shown in FIGS. 2A and 3A-B. Each blade 24, like each marker 22, is formed of a material that is opaque to one or more medical imaging technologies. Similar to above, the term radiopaque is used to describe blade 24 as, without limitation, being opaque to X-rays. Each blade 24 may also be visually opaque. Blade 24 defines a second plane B-B (FIGS. 2A, 3B). Each blade 24 is depicted in FIG. 2A as an elongated element housed within interior portion 21. Aside from markers 22 and blade 24, the remainder of interior portion 21 may be empty and/or open so as to enhance the transparency of device 10. Each blade 24 has at least one perimeter coaxial with shaft 20. As depicted in FIG. 3B, for example, blade 24 has a rectangular perimeter centered on shaft axis X-X, said perimeter having a short length and a long length, wherein the long length is parallel to and centered on axis Y-Y and the short length is parallel to and centered on an axis Z-Z that is transverse with axis Y-Y.

Second plane B-B is used to establish a relative difference between a reference position on shaft 22 and an operative end 52 (FIG. 2B) of needle 50 with respect to shaft axis X-X. In some embodiments, second plane B-B may be parallel to shaft axis X-X and defined by superimposing a top edge of blade 24 with a bottom edge of blade 24. Alternatively, if needle 50 has been received in needle guide 30, as described below, then second plane B-B may be defined by superimposing blade 24 with needle 50. The reference position on shaft 22 may be defined in relation to one of the plurality of markers 22. Each marker 22 may, for example, be spaced at regular intervals along shaft axis X-X to provide a relative difference between one of said markers 22 and operating end 52 of needle 50. Hash marks, radiopaque or radiolucent, may be provided on shaft 20 between each marker 22 for additional relativity.

Figure 2B:
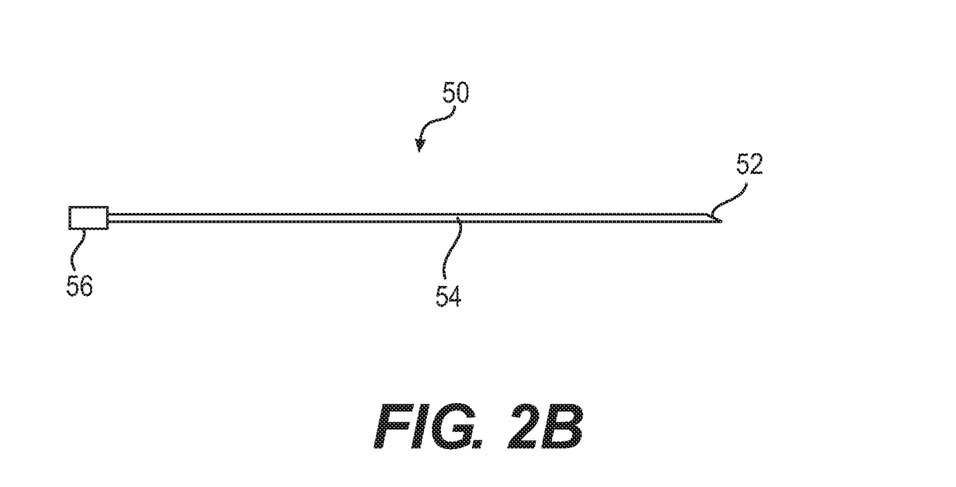
FIG. 2B depicts a needle for use with the device of FIG. 2A.
Figure 4A:
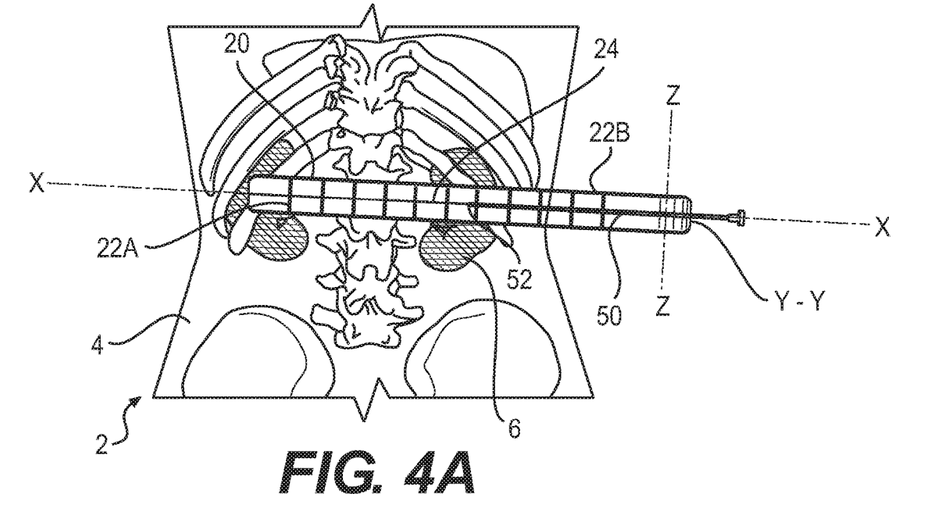
FIG. 4A depicts a top view of the device of FIG. 2A adjacent a body, and the needle of FIG. 2B inside of the body.
Figure 4B:
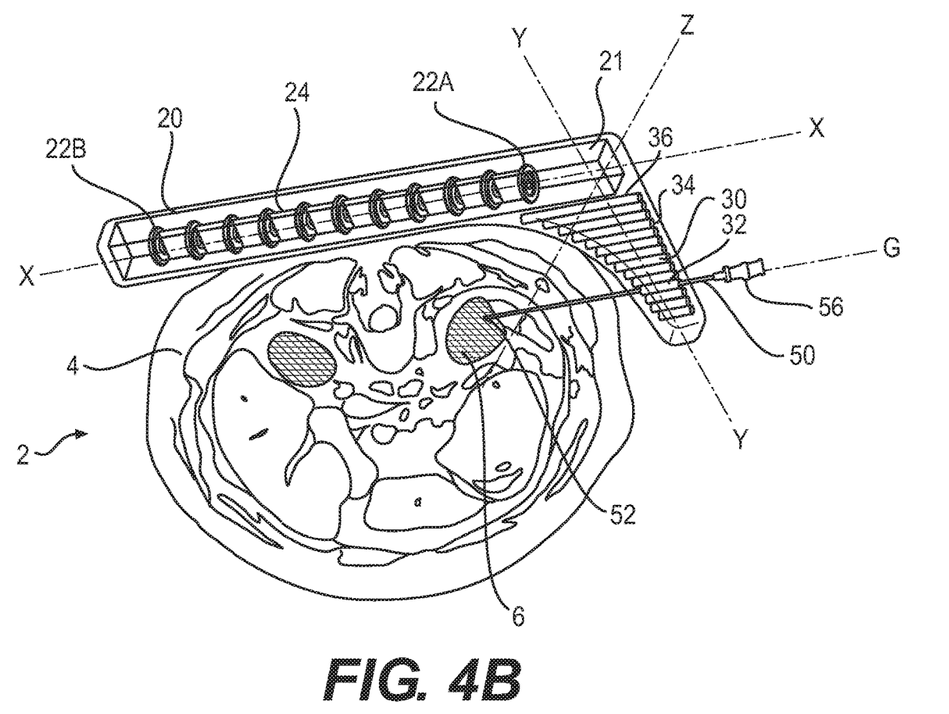
FIG. 4B depicts a perspective view of the device of FIG. 2A adjacent a body, and the needle of FIG. 2B inside of the body.
Figure 5:
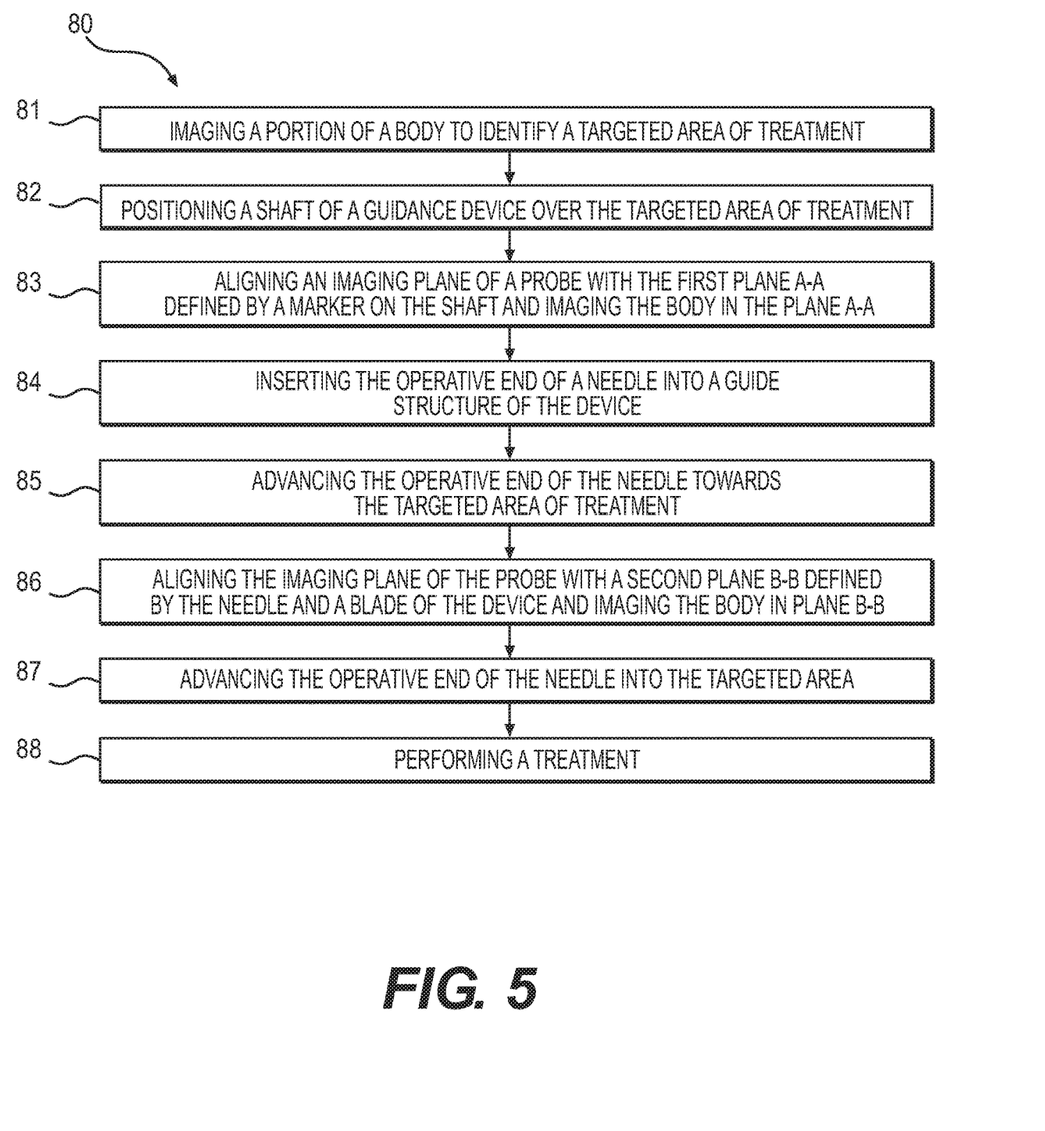
FIG. 5 depicts a set of exemplary method steps.

Needle guide 30 of FIG. 2A has at least one guide structure 32 offset from shaft axis X-X along needle guide axis Y-Y. Each structure 32 is adapted to receive needle 50 in a direction parallel to shaft axis X-X. An exemplary needle 50 is depicted in FIG. 2B as having a distal or operative end 52, a shaft 54, and a proximal or working end 56. As depicted in FIGS. 2A and 4B, each at least one guide structure 32 has a guiding axis G-G that is parallel to shaft axis X-X and transverse with needle guide axis Y-Y. Each guide structure 32 has an entry 34 sized to receive needle 50 along guiding axis G-G, and a sidewall 36 extending along guiding axis G-G to maintain needle 50 in second plane B-B. For example, sidewall 36 may be configured to stabilize needle 50 as it is advanced into a body 2 (FIG. 4B) along guiding axis G-G. Each entry 34 may be circular and each sidewall 36 cylindrical. The spacing between each structure 32 may vary. For example, the guiding axis G-G of each structure 32 may be offset from the next along axis Y-Y by a regular distance, thereby allowing the surgeon to more accurately locate needle 50 within first plane A-A, relative to shaft axis X-X.

As illustrated in FIG. 2A, for example, device 10 has a body facing surface 40 comprised of portions of shaft 20 and needle guide 30. A first body facing surface 42 is located on one side of the perimeter of shaft 20. Surface 42 is depicted in FIG. 2A as a substantially planar surface parallel to shaft axis X-X. Needle guide 30 has a second body facing surface 44 depicted in FIG. 2A as a substantially planar surface parallel to needle guide axis Y-Y. First and second surfaces 42 and 44 intersect and are joined by a third body facing surface or fillet 46, thereby giving device 10 an "L" shape in FIG. 2A. In some embodiments body facing surface 40 may be form fit to a portion 4 of body 2 (FIG. 4B) by further contouring the first, second, and/or third surfaces 42, 44, and 46.

An exemplary method 80 of using device 10 is now described with reference to FIGS. 1-5, wherein device 10 is utilized to guide an operative end 52 of needle 50 (FIG. 2B) into a targeted area of treatment 6 within a body 2 (FIG. 4B). Method 80 may comprise an initial step 81 (FIG. 5) of imaging a portion 4 of body 2 to identify a targeted area of treatment 6. For example, as shown in FIG. 4A, portion 4 may be a torso of body 2 that has been imaged in the coronal plane to locate area of treatment 6, in this instance, a kidney. The exterior surface of body 2 may be marked to indicate an initial position for shaft 22. Another method step 82 (FIG. 5) may comprise positioning shaft 20 over the targeted area of treatment 6, as shown in FIG. 4A, wherein shaft 20 has been positioned over the located kidney. Blade 24 of shaft 20 may be aligned with said markings. Step 82 may further comprise moving device 10 distally towards body 2 until a substantial portion of body facing surface 40 is adjacent portion 4 of body 2. Device 10 may come to rest on body 2.

With shaft 22 in position, method 80 may further comprise a step 83 (FIG. 5) for aligning the imaging plane of probe 3 with a first plane A-A defined by at least two of markers 22, such as markers 22A and 22B; and imaging body 2 in plane A-A. Multiple images may be required to align probe 3 with plane A-A. For example, a series of images may be required to superimpose markers 22A and 22B along shaft axis X-X, wherein each successive image indicates a direction of movement for either probe 3 or device 10, such the markers 22A and 22B are superimposed by making the indicated movements. Another method step may comprise securing device 10 against body 2 with, for example, surgical tape or like securing element. Imaging body 2 in first plane A-A allows the surgeon to determine the depth of targeted area of treatment 6 relative to needle guide axis Y-Y. Other method steps may comprise a step 84 (FIG. 5) for inserting the operative end 52 of needle 50 into one of the guide structures 32; and a step 85 (FIG. 5) for advancing the operative end 52 towards targeted area of treatment 6. Operative end 52 may be advanced through intermediate layers of body 2, such as bone, cartilage, tissue, and the like, any of which may cause needle 50 to drift relative to guiding axis G-G. As noted above, sidewall 36 stabilizes needle 50 to minimize drift. The interaction between surface 40 and body 2 may further minimize drift by providing additional leverage for sidewall 50.

Operative end 52 is guided into targeted treatment area 6 so as to avoid unwanted tissue damage. Thus, another method step 86 (FIG. 5) may comprise aligning the imaging plane of probe 3 with a second plane B-B defined, for example, by blade 24 and needle 50; and imaging the body in plane B-B. Blade 24, like markers 22, is radiopaque; thus, as before, successive images may be taken, each indicating a direction of movement, such that blade 24 and needle 50 are superimposed by moving probe 3 as indicated. In contrast to above, the position of device 10 may remained fixed in step 86 to avoid parallax error. Imaging body 2 in plane B-B allows the surgeon to determine how far to advance the operative end 52 of needle 50 into the targeted area of treatment 6 along guiding axis G-G. For example, an image of body 2 in plane B-B may show the location of operative end 52 relative to area of treatment 6 and any one of markers 22, or any hash marks located between any two markers 22. These reference positions are used to guide operative end 52. Accordingly, other method steps may comprise a step 87 (FIG. 5) for advancing the operative end 52 of needle 50 into targeted area 6; and a step 88 (FIG. 5) for performing a treatment.

Many elements of device 10 and method 80 may be modified without departing from the present disclosure. For example, in FIGS. 2A and 4B, device 10 is depicted as an asymmetrical element, with a single needle guide 30. Device 10 might alternatively have a pair of needle guides 30, each of which may be symmetrically arranged on opposite ends of device 10. In a symmetrical embodiment of device 10, for example, body facing surface 40 may be configured to wrap partially around body 2 (FIG. 4B), thereby allowing the surgeon to treat both kidneys without moving device 10.

Shaft 20 of FIG. 4B, for example, has a substantially rectangular perimeter. Any perimeter shape is possible, open or closed, including triangular, circular, or the like. The perimeter of any marker 22 may be modified accordingly, and need not be circular nor confined within interior portion 21 of shaft 20 (FIG. 2A). Shaft 20 has been described as rigid, but this is not required. For example, a portion of shaft 20 may be flexibly conformable with body 2 so as to hold device 10 in position. Body facing surface 40 of shaft 22 (FIGS. 2A, 4B) may have a flexible layer that is conformable against body 2. Instead of surgical tape or the like, surface 40 may have an adhesive layer that allows for direct securement to body 2. Markers 22 have been depicted in FIG. 3A has having a narrow width along shaft axis X-X. Any width is contemplated, for example, the width of markers 22 may be increased along axis X-X to further obfuscate the view down shaft axis X-X when shaft 22 is out of alignment. Plurality of markers 22 may, thus, be embodied as a single marker 22 of sufficient width, wherein the inner and out perimeters of said single marker are superimposed to define plane A-A. At least the outer perimeter may be visually opaque. The width and/or perimeter of blade 24 (FIG. 3B) may be similarly varied. For example, at least one blade 24 may be embodied as at two blades extending along shaft axis X-X, such that second plane B-B is defined by locating needle 50 therebetween. The perimeter of any blade 24 may be rectangular, diamond shaped, elliptical, or any other shape, which may also be visually opaque.

Needle guide 30 may also be modified. For example, guide 30 is depicted in FIG. 2A has having a plurality of guiding structures 32, each being rigidly attached thereto. Alternatively, guide 30 may have a single guide structure 32 that is moveable along needle guide axis Y-Y within a track mounted in guide 30. Guide structure 32 has been described as having an entry 34 with a circular opening (FIG. 3B). This is not required. For example, entry 34, and corresponding sidewall 36 (FIG. 4B), may have an open perimeter, such as a channel or channel bore, extending along guiding axis G-G.

Any step of method 80 described above may be modified to accommodate these alternative embodiments of device 10, or any other variations described herein.

Figure 6:
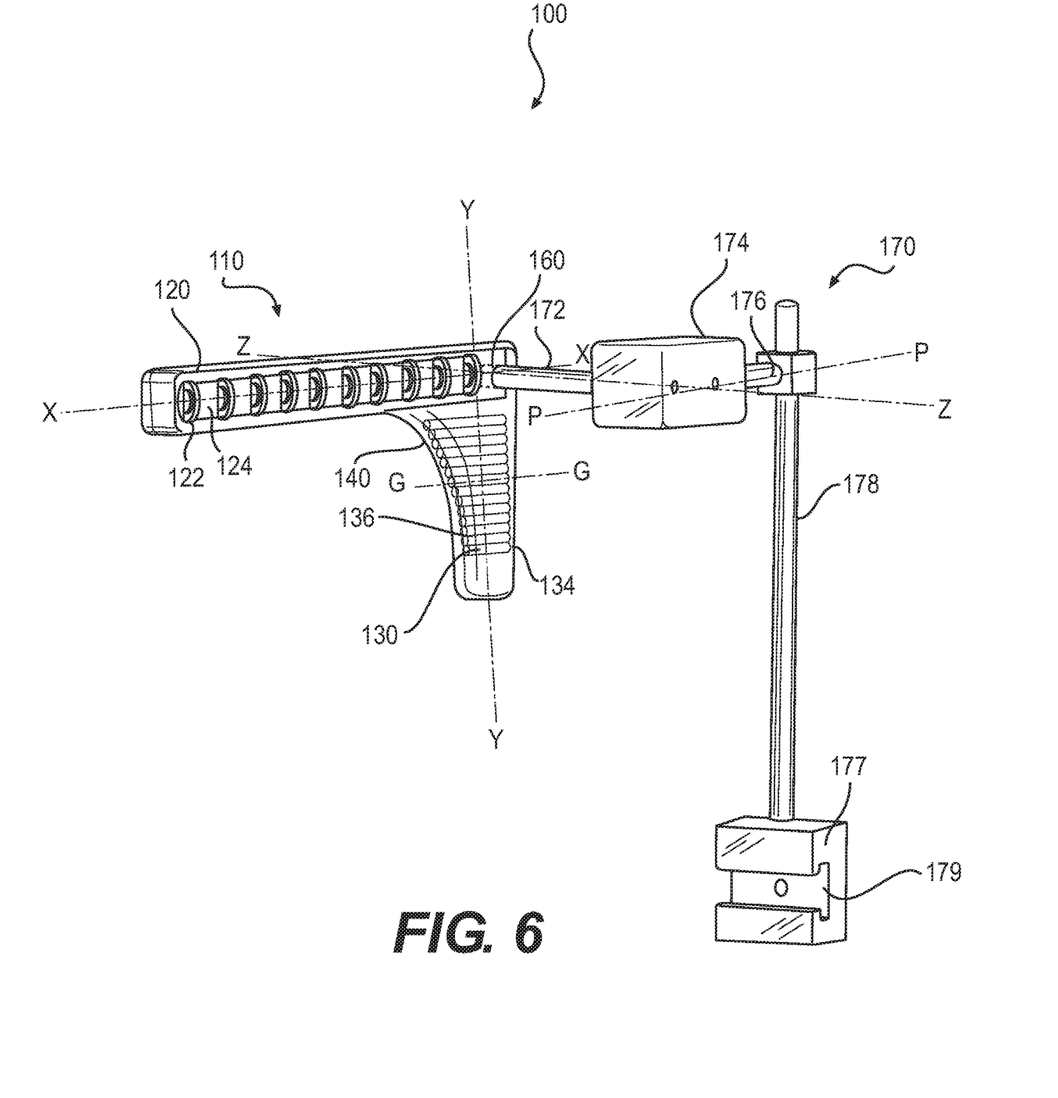
FIG. 6 depicts a perspective view of an exemplary system according to the present disclosure, wherein the system comprises a guidance device and a positioning arm.
Figure 7:
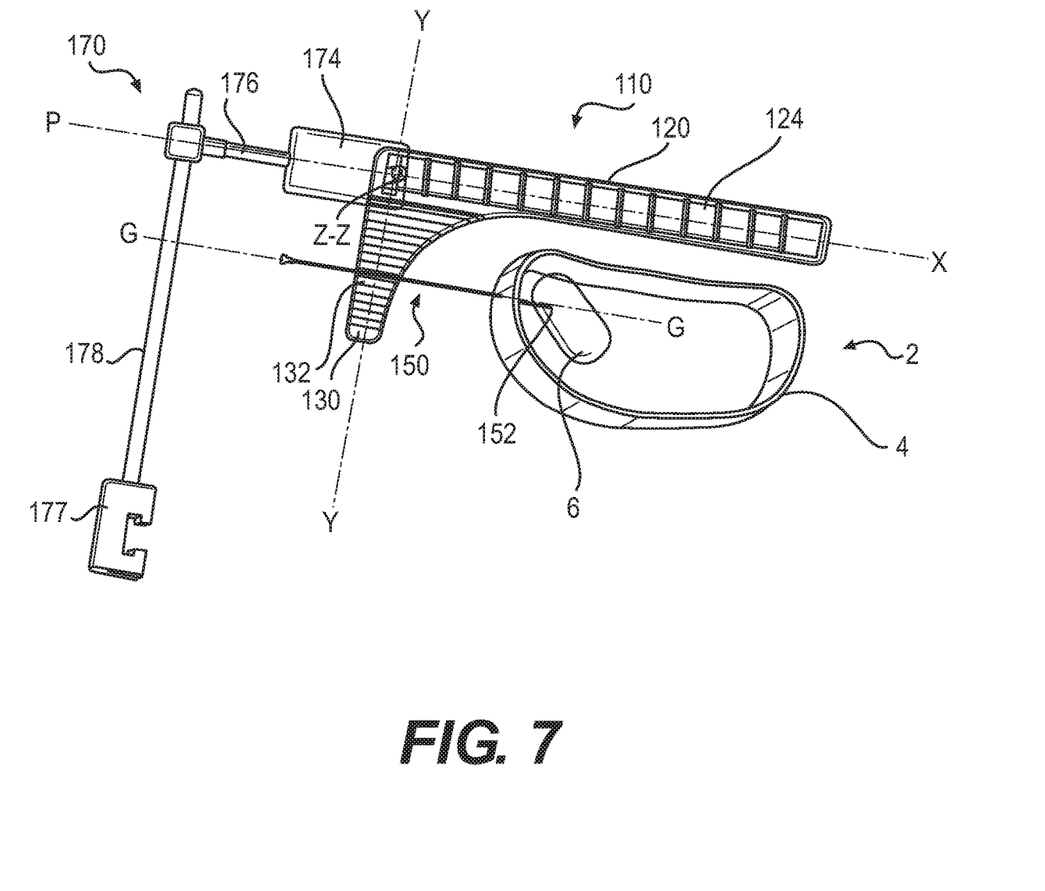
FIG. 7 depicts a perspective view of the system of FIG. 6 with a body facing surface of the guidance device proximate to a body and a needle in the body.
Figure 8A:
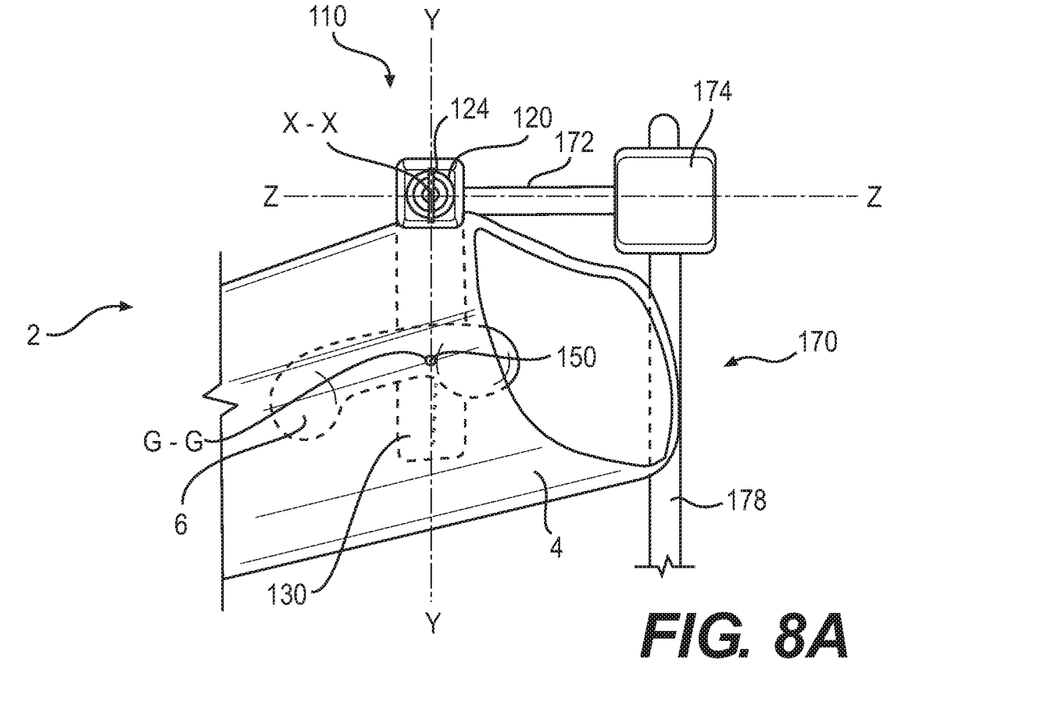
FIG. 8A depicts a perspective view of the system of FIG. 7 with a body facing surface of the guidance device adjacent a body.
Figure 8B:
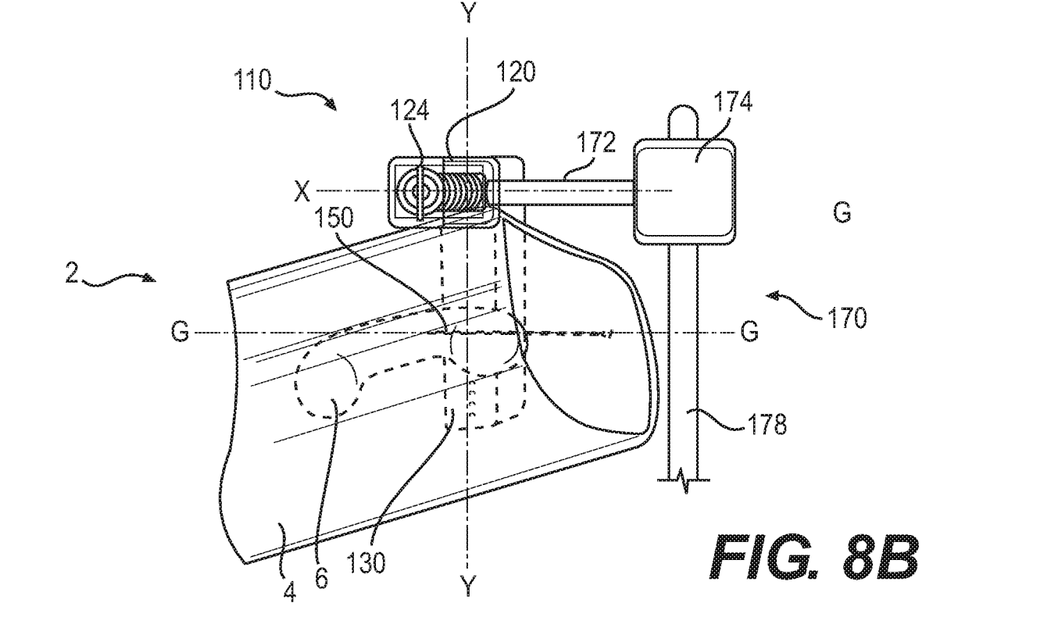
FIG. 8B depicts the view of FIG. 8A from a different perspective.
Figure 9A:
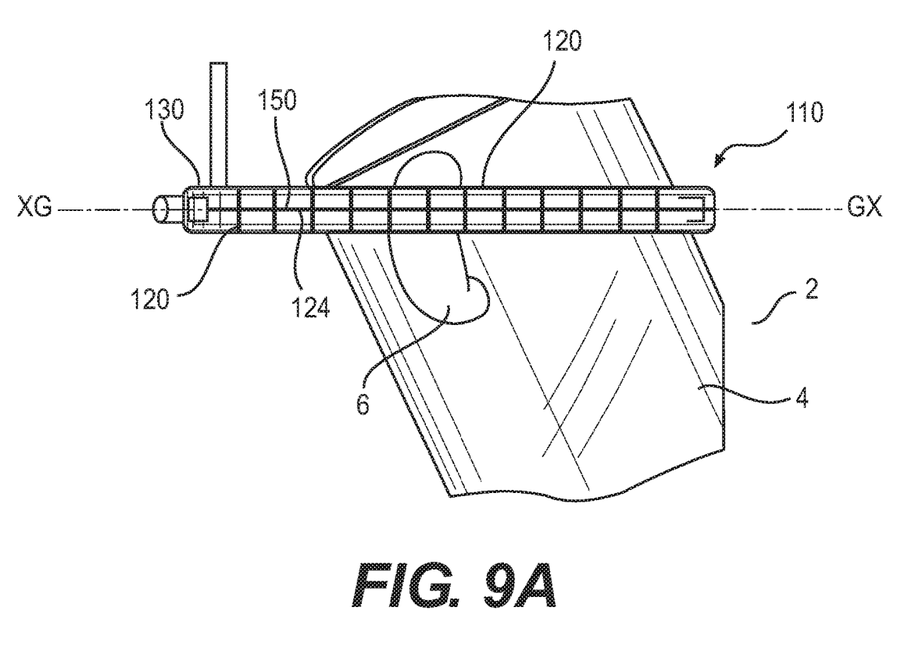
FIG. 9A depicts a perspective view of the system of FIG. 6 with a body facing surface of the guidance device adjacent a body.
Figure 9B:
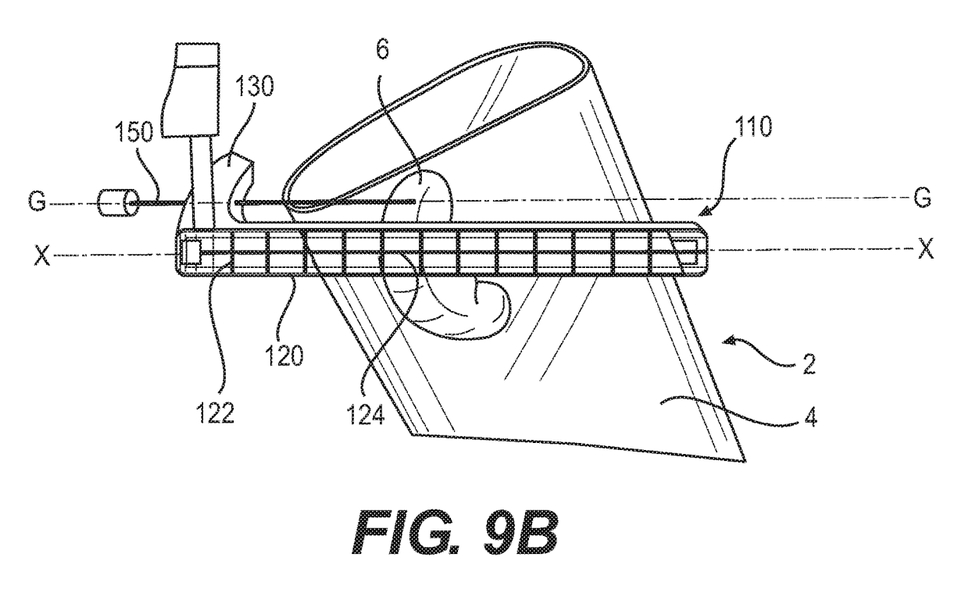
FIG. 9B depicts the view of FIG. 8B from a different perspective.
Figure 10:
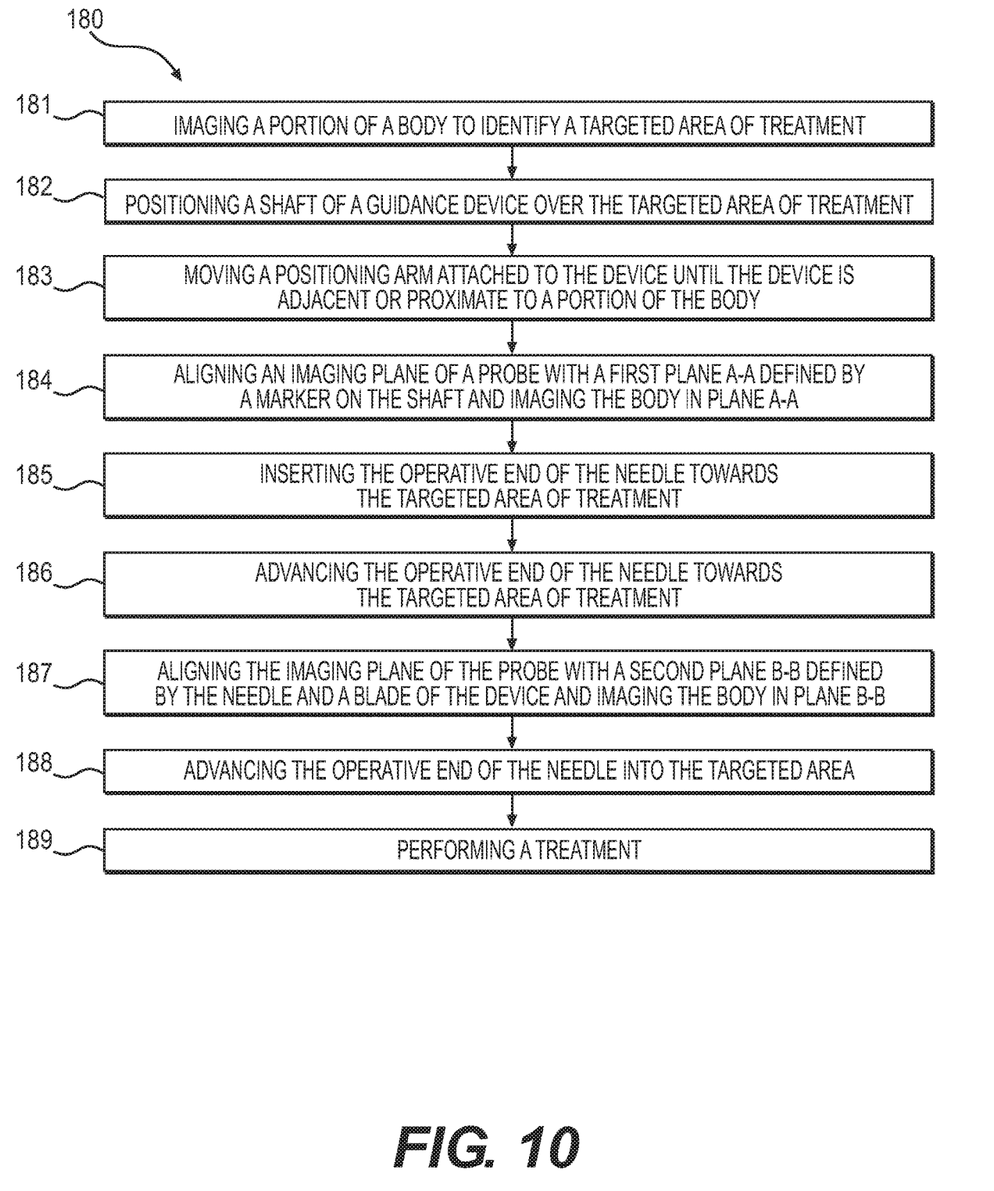
FIG. 10 depicts a set of exemplary method steps.

Another embodiment of the present disclosure is depicted in FIGS. 6-7 as a system 100 comprising of a guidance device 110 and a positioning arm 170. Guidance device 110 is similar to device 10; thus, wherever possible, like element numbers have been used to described each corresponding element of device 110. For example, guidance device 110, like device 10, has a shaft 120 extending along shaft axis X-X. Shaft 120 has at least two markers 122 spaced along a shaft axis X-X, and a blade 124 extending along shaft axis X-X. A needle guide 130 extends away from shaft 122 along a needle guide axis Y-Y that is transverse, or even perpendicular, with shaft axis X-X. Similar to above, needle guide 130 has at least one guide structure 132 offset from shaft axis X-X along needle guide axis Y-Y, each structure 132 having an entry 134 and a sidewall 136 with a guiding axis G-G parallel with shaft axis X-X.

In contrast to above, device 110 further comprises an interface 160 that is engageable with a positioning arm 170 of system 100. As shown in FIGS. 6-7, interface 160 is a depression located at the intersection of shaft axis X-X and needle guide axis Y-Y, and secured to an end of a first segment 172 of arm 170 by any known securing means, including an adhesive, a thread, a set screw, or the like. First segment 172 extends away from interface 160 along an axis Z-Z that is transverse to axes X-X and Y-Y. First segment 172 is rotatably attached to a junction box 174 using a set of gears, a ratchet assembly, or like mechanism. Box 174 allows segment 172, and thus device 110, to be rotated about axis Z-Z, for example, to define first plane A-A. A second segment 176 of positioning arm 170 is rotatably attached to junction box 174 along a pivot axis P-P that is substantially parallel to shaft axis X-X, thereby allowing device 110 to be further rotated about axis P-P, for example, to define second plane B-B.

Second segment 176 extends from junction box 174 along pivot axis P-P for attachment to riser 178, which extends from a rigid surface attachment point 177. Attachment point 177 is engageable with a rigid surface, such as an operating table 5 (e.g., FIG. 1). As shown in FIGS. 6-7, for example, attachment point 177 has an interior surface 179 configured for engagement with an attachment rail 7 (e.g., FIG. 1) mounted on table 5. Any alternative form of attachment may be provided, including a clamp or like mechanism. Second segment 176 is slidably attached to riser 178 so that the position of device 110 relative to table 5 may be adjusted. Any form of attachment between segment 176 and riser 178 is contemplated, such as a split collar with a set screw, as shown in FIGS. 6-7.

An exemplary method 180 of using system 100 is now described with reference to FIGS. 6-10. Similar to above, device 110 may be used in system 100 to guide an operative end 152 of needle 150 into a targeted area of treatment 6 within a body 2 (FIG. 7). Method 180 may comprise the initial step 181 (FIG. 10) of imaging a portion 4 of body 2 to identify a targeted area of treatment 6. Another method step 182 (FIG. 10) comprises positioning shaft 122 over the targeted area of treatment 6, as shown in FIG. 7, wherein shaft 22 has been positioned over the located kidney. This step may be accomplished by moving positioning arm 170. For example, arm 70 may be moved from a retracted position to an extended position so as to position shaft 22 accordingly. Another method step 183 (FIG. 10) may comprise moving positioning arm 170 so as to move device 110 towards body 2 until a substantial portion of body facing surface 140 is adjacent or proximate to portion 4 of body 2, as in FIGS. 8A-9B. Alternatively, because device 110 is supported by arm 170, shaft 120 may be hovered over body 2 to accommodate varying body types, including an obese body type that lacks the relatively flat surfaces depicted in FIG. 7.

After positioning shaft 122, another method step 184 (FIG. 10) may comprise aligning the imaging plane of probe 3 within a first plane A-A defined by markers 122 and imaging body 2 in plane A-A. This step may be accomplished by moving positioning arm 170. For example, first plane A-A may be defined by moving first segment 172 about axis Z-Z and/or second segment 176 about axis P-P until device 110 has been moved from the misaligned position shown in FIG. 8A, wherein markers 122 are not superimposed, to the aligned position of FIG. 8B, wherein markers 122 are superimposed. Other method steps may comprise a step 185 (FIG. 10) for inserting an operative end 152 of needle 150 into one of the guide structures 132; and a step 186 (FIG. 10) for advancing operative end 152 towards targeted area of treatment 6. System 100 may be further configured to prevent needle drift by firming up the connection between device 110, first segment 172, junction box 174, second segment 176, and riser 178.

Another method step 187 (FIG. 10) may comprise aligning the imaging plane of probe 3 with a second plane B-B defined, for example, by superimposing blade 124 with needle 150, and imaging the body in second plane B-B. This step may be accomplished by moving positioning arm 170. For example, similar to above, second plane B-B may be defined by rotating device 110 about pivot axis P-P until it has been moved from the misaligned position shown in FIG. 9A, wherein blade 124 is not superimposed with needle 150; to the aligned position of FIG. 9B, wherein blade 124 and needle 150 are superimposed. A reference position on shaft 122 may be used to guide operative end 152. Other method steps may comprise a step 188 (FIG. 10) for advancing the operative end 152 of needle 150 into targeted area 6; and a step 189 (FIG. 10) for performing a treatment.

Many elements of system 100 and method 180 may be modified without departing from the scope of the present disclosure. For example, positioning arm 170 has been described as being attached to device 110 along an axis Z-Z, as shown in FIGS. 6-7. This is optional as, in some embodiments, arm 170 may be attached to device 110 along shaft axis X-X, needle guide axis Y-Y, or some other position. The various elements of arm 170 have been described as moveable. These elements may be moved physically, in response to a manual force applied by the surgeon; or mechanically, by one or more actuators or motors attached to arm 170. For example, junction box 174 (FIGS. 6-7) may have a motor configured to rotated first and second segments 172 and 176, while riser 178 is attached to a linear actuator configured to move second segment 176 relative to table 5, thereby allowing arm 170 to move, as needed, in order to define planes A-A and B-B in the described manner. Any such actuators or motors may be attached to processor configured to remember the exact position of arm 170 and replicate said position on command.

As before, any step of method 180 may be modified to accommodate any of these alternative embodiments of system 100, if needed.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the present disclosure is not to be considered as limited by the foregoing description.

I claim:

1. A guidance device for a percutaneous nephrolithotomy procedure, the device comprising:
   a shaft extending along a shaft axis, the shaft including:
      a plurality of markers spaced along the shaft axis; and
      a blade extending along the shaft axis; and
   a needle guide extending away from the shaft along a needle guide axis transverse with the shaft axis, the needle guide including a plurality of guide structures offset from the shaft axis along the needle guide axis, each of said guide structures being adapted to receive a needle in a direction parallel to the shaft axis,
   wherein the guide structures are arranged such that the guide structures each have a guiding axis that is transverse to the needle guide axis, and
   wherein lengths of the guide structures decrease along the needle guide in a direction away from the shaft such that the needle guide includes a curved body facing surface configured to be placed against a body to position the guidance device relative to the body for the percutaneous nephrolithotomy procedure.

2. The device of claim 1, wherein the shaft and needle guide are made of a radiolucent material, and wherein each of the plurality of markers is made of a radiopaque material.

3. The device of claim 2, further comprising a plurality of radiopaque hash marks disposed a regular intervals between each of plurality of markers.

4. The device of claim 1, wherein the shaft includes a substantially rectangular perimeter coaxial with the shaft axis and a body facing surface located on a side of said perimeter, the side being offset from the shaft axis along the needle axis.

5. The device of claim 1, wherein the shaft has a hollow interior portion and the blade and the plurality of markers are mounted in the hollow portion.

6. The device of claim 5, wherein the shaft has as a first end and a second end, the first end being opposite of the second end along the shaft axis, and wherein one of the plurality of markers is located at each of the first and second ends, such that a first plane is defined by aligning each of said markers along the shaft axis.

7. The device of claim 1, wherein each of the guide structures comprises:
an entry with a perimeter that is coaxial with the guiding axis and sized to receive a needle along the guiding axis; and
an interior sidewall that is coaxial with the guiding axis and adapted to guide the needle along the guiding axis,
wherein the guiding axis of each guide structure is parallel with the shaft axis.

8. The device of claim 7, wherein the plurality of guide structures comprises a plurality of guide structures spaced apart at regular intervals along the needle guide axis in a single column, each interval being marked by a hash mark.

9. A guidance system for a percutaneous nephrolithotomy procedure, the system comprising:
a guidance device for the percutaneous nephrolithotomy procedure including:
a shaft extending along a shaft axis, the shaft including:
at least one marker with a perimeter coaxial with the shaft axis, said perimeter including a width extending along the shaft axis; and
a blade extending along the shaft axis,
wherein the shaft includes a body facing surface extending parallel to the shaft axis;
a needle guide extending away from the shaft along a needle guide axis transverse with the shaft axis, the needle guide including a plurality of guide structures offset from the shaft axis along the needle guide axis, the guide structures each being adapted to receive a needle along a guiding axis parallel to the shaft axis, wherein lengths of the guide structures decrease along the needle guide in a direction away from the shaft such that the needle guide includes a curved body facing surface that intersects the body facing surface of the shaft to form a continuous body facing surface; and
a positioning arm engageable with a interface portion of the guidance device, the arm being adapted to move the guidance device relative to a body,
wherein the positioning arm is movable to place the continuous body facing surface against the body for the percutaneous nephrolithotomy procedure.

10. The system of claim 9, wherein the shaft, the needle guide, and the positioning arm are made of a radiolucent material, and wherein the at least one marker and the blade are made of a radiopaque material.

11. The system of claim 9, wherein the shaft includes a substantially rectangular perimeter coaxial with the shaft axis and the body facing surface of the shaft is located on a side of said perimeter.

12. The system of claim 11, wherein the positioning arm is adapted to fix the position of the guidance device relative to the body.

13. The system of claim 11, further comprising one or more actuators attached to the positioning arm, each actuator being configured to move said arm.

14. The device of claim 9, wherein the continuous body facing surface includes a flexible layer that is configured to be positioned against the body.

15. The device of claim 9, wherein the continuous body facing surface includes an adhesive layer that is configured to secure the body facing surface to the body.

16. A guidance device for a percutaneous nephrolithotomy procedure, the device comprising:
a shaft extending along a shaft axis, the shaft including:
a plurality of markers spaced along the shaft axis; and
a blade extending along the shaft axis; and
a needle guide extending away from the shaft along a needle guide axis transverse with the shaft axis, the needle guide including a plurality of guide structures offset from the shaft axis along the needle guide axis, each of said guide structures being adapted to receive a needle in a direction parallel to the shaft axis,
wherein the guide structures are arranged in a single column along the needle guide, and
wherein lengths of the guide structures decrease along the needle guide in a direction away from the shaft such that the needle guide includes a curved body facing surface configured to be placed against a body to position the guidance device relative to the body.

17. The device of claim 16, wherein the shaft and needle guide are made of a radiolucent material, and wherein each of the plurality of markers is made of a radiopaque material.

18. The device of claim 17, further comprising a plurality of radiopaque hash marks disposed a regular intervals between each of plurality of markers.

19. The device of claim 16, wherein the body facing surface includes a flexible layer that is configured to be positioned against the body.

20. The device of claim 16, wherein the body facing surface includes an adhesive layer that is configured to secure the body facing surface to the body.

* * * * *